US011351383B2

United States Patent
Sambelashvili et al.

(10) Patent No.: US 11,351,383 B2
(45) Date of Patent: Jun. 7, 2022

(54) LEFT VENTRICULAR CAPTURE AND SYNCHRONIZATION VERIFICATION USING A SINGLE MULTI-ELECTRODE CORONARY SINUS LEAD

(71) Applicant: Medtronic, Inc., Minneapolis, MN (US)

(72) Inventors: Aleksandre Sambelashvili, Maple Grove, MN (US); Yong Cho, Excelsior, MN (US); Jeffrey Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 212 days.

(21) Appl. No.: 15/966,960

(22) Filed: Apr. 30, 2018

(65) Prior Publication Data
US 2019/0329046 A1    Oct. 31, 2019

(51) Int. Cl.
| | | |
|---|---|---|
| *A61N 1/37* | (2006.01) | |
| *A61N 1/05* | (2006.01) | |
| *A61N 1/372* | (2006.01) | |
| *A61N 1/39* | (2006.01) | |
| *A61B 5/352* | (2021.01) | |

(52) U.S. Cl.
CPC ......... *A61N 1/3712* (2013.01); *A61N 1/0573* (2013.01); *A61N 1/3702* (2013.01);
(Continued)

(58) Field of Classification Search
None
See application file for complete search history.

(56) References Cited

U.S. PATENT DOCUMENTS

| 5,117,824 A | 6/1992 | Keimel et al. |
|---|---|---|
| 6,393,316 B1 | 5/2002 | Gillberg et al. |

(Continued)

FOREIGN PATENT DOCUMENTS

| WO | 2009114360 A1 | 9/2009 |
|---|---|---|
| WO | 2017011659 A1 | 1/2017 |

OTHER PUBLICATIONS (PCT/US2019/029652) PCT Notification of Transmittal of the International Search Report and the Written Opinion of the International Searching Authority, dated Nov. 13, 2019, 10 pages.
(Continued)

*Primary Examiner* — Erica S Lee
(74) *Attorney, Agent, or Firm* — Mueting Raasch Group

(57) ABSTRACT

A method and implantable medical device system for delivering a left ventricular (LV) cardiac pacing therapy via a single-pass coronary sinus lead and sensing far-field cardiac signals via one or more far-field sensing vectors formed between the plurality of electrodes. Beat morphologies corresponding to the far-field cardiac signals are determined, and a beat morphology match between each of the far-field beat morphologies and an intrinsic beat morphology template is determined so that one of loss of LV capture, pseudo fusion and loss of synchrony is determined in response to the determined beat morphology match. One of a loss of capture adjustment, a pseudo fusion adjustment, and a resynchronization adjustment is performed in response to the determined one of loss of LV capture, pseudo fusion and loss of synchrony in response to the determined beat morphology match to generate an adjusted LV cardiac pacing therapy.

19 Claims, 7 Drawing Sheets

(52) U.S. Cl.
CPC ....... *A61N 1/37223* (2013.01); *A61N 1/3937* (2013.01); *A61B 5/352* (2021.01)

(56) References Cited

U.S. PATENT DOCUMENTS

| | | | |
|---|---|---|---|
| 6,738,669 B1* | 5/2004 | Sloman | A61N 1/3712 607/15 |
| 6,907,386 B1 | 6/2005 | Liggesmeyer | |
| 7,062,315 B2 | 6/2006 | Koyrakh et al. | |
| 8,126,551 B2 | 2/2012 | Perschbacher et al. | |
| 9,095,720 B2* | 8/2015 | Keel | A61N 1/3684 |
| 2006/0271119 A1* | 11/2006 | Ni | A61N 1/3627 607/9 |
| 2012/0136263 A1* | 5/2012 | Prakash | A61B 5/11 600/510 |
| 2013/0053918 A1 | 2/2013 | Sambelashvili et al. | |
| 2013/0197599 A1 | 8/2013 | Sambelashvili et al. | |
| 2014/0046389 A1* | 2/2014 | Anderson | A61N 1/0573 607/4 |
| 2014/0276151 A1* | 9/2014 | Xi | A61B 5/04012 600/508 |

OTHER PUBLICATIONS

Office Action from U.S. Appl. No. 15/967,015 dated Jul. 22, 2020, 7 pages.
Office Action from U.S. Appl. No. 15/967,015 dated Nov. 12, 2020, 6 pages.

* cited by examiner

LEFT VENTRICULAR CAPTURE AND SYNCHRONIZATION VERIFICATION USING A SINGLE MULTI-ELECTRODE CORONARY SINUS LEAD

FIELD

The present disclosure pertains to cardiac pacing methods and systems, and, more particularly, to a method and apparatus for delivering cardiac pacing therapy in an implantable cardiac therapy device system having only a single multi-electrode coronary sinus lead.

BACKGROUND

The activity of a normal, healthy heart involves the synchronized contraction of the atria and ventricles of the heart. Blood is received into the atria, which contract, forcing the blood into the ventricles. Subsequent contraction of the ventricles then causes the blood to be pumped through the body and eventually returned to the atria. The contractions of the chambers of the heart are caused by coordinated electrical activation of portions of the cardiac muscle.

The heartbeat cycle begins with the generation of an electrical impulse by a bundle of fibers located in the sinoatrial node of the heart, near the upper portion of the right atrium at the entrance to the superior vena cava. This impulse propagates across the atria, stimulating the atrial muscles and causing the atrial contraction, which forces blood into the ventricles. An atrial contraction is manifested as the so-called "P-wave" in an electrocardiographic signal. The electrical impulse conducted through the atrial muscle is then received at the partition wall immediately beside the valve between the right atrium and right ventricle, at the atrio-ventricular or A-V node. The A-V node introduces a slight delay in the transmission of the electrical impulse to the ventricles. This A-V delay is typically on the order of 100 milliseconds. After the A-V delay, the electrical impulse is conducted to the ventricles, causing the ventricular contraction which is manifested as the "QRS complex" of an electrocardiographic signal. Subsequent repolarization and relaxation of the ventricular muscles occurs at the end of the cardiac cycle, which is manifested as the "T-wave" portion of an electrocardiographic signal.

For patients in which the above-described conduction of electrical impulses through the cardiac muscle is somehow impaired, a pacemaker can provide an artificial electrical stimulus where no natural electrical impulse is present. Thus, for example, a ventricular pacemaker can function to cause ventricular contractions in patients in which the natural electrical cardiac impulse is, for some reason, not transmitted across the A-V node. It is important, however, that any artificial stimulating pulses be delivered at appropriated times, so that proper synchronization of atrial and ventricular action is maintained. In addition, it is known that electrical impulses being delivered to the cardiac muscle during the repolarization phase at the end of the cardiac cycle can cause the onset of tachyarrhythmias. It is therefore important that the pacemaker be prevented from delivering stimulating pulses during the T-wave.

In order to maintain A-V synchrony, and to prevent delivery of pacing pulses at undesirable times, pacemakers are preferably capable of detecting either atrial activity, ventricular activity, or both, as manifested by the P-wave and QRS complex (or more typically the R-wave), respectively, via atrial and ventricular cardiac electrogram signals sensed by the pacemaker.

Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart and inhibit or trigger delivery of pacing stimuli to the heart based on the occurrence and recognition of sensed intrinsic electrical events.

The beat of the heart is controlled by the sinoatrial node, a group of conductive cells located in the right atrium near the entrance of the superior vena cava. The depolarization signal generated by the sinoatrial node activates the atrioventricular node. The atrioventricular node briefly delays the propagation of the depolarization signal, allowing the atria to drain, before passing the depolarization signal to the ventricles of the heart. The coordinated contraction of both ventricles drives the flow of blood through the body of a patient. In certain circumstances, the conduction of the depolarization signal from the atrioventricular node to the left and right ventricles may be interrupted or slowed. This may result in a dyssynchrony in the contraction of the left and right ventricles, which may lead to heart failure or death.

Cardiac resynchronization therapy (CRT) may correct the symptoms of electrical dyssynchrony by providing pacing therapy through medical electrical leads to one or both ventricles or atria to encourage earlier activation of the left or right ventricles. By pacing the contraction of the ventricles, the ventricles may be controlled so that the ventricles contract in synchrony.

Cardiac resynchronization pacing devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. Delivering electrical stimuli that causes the ventricle to respond is commonly referred to as capturing a ventricle. For a variety of reasons, cardiac pacing systems may not achieve effective capture of a ventricle. For example, a pacing lead and/or electrode may not be placed in an optimal location. Sensed atrioventricular delay (SAV), paced atrioventricular delay (PAV), right ventricular pre-excitation may also affect whether a ventricle is effectively captured. Exemplary reasons for ineffective capture include a sensed atrioventricular delay (SAV) that is too long, a paced atrioventricular delay (PAV) that is too long, and RV pre-excitation are typically addressed through adjusting delivery of the electrical stimuli to the ventricle. Other exemplary reasons for ineffective capture may include occurrence of atrial fibrillation (AF), a medical electrical lead placed in scar tissue, loss of capture due to lead dislodgement, atrial under sensing, a rate above an upper tracking rate, and the right and left ventricular leads are too close. Additionally, after the medical device has been implanted, migration or dislodgement of the pacing lead may occur, resulting in ineffective capture.

One form of CRT is fusion pacing, which typically involves left ventricle (LV) only pacing with an electrode on the LV medical electrical lead in coordination with the intrinsic right ventricle (RV) activation. Effective fusion requires, for example, that the timing of the LV pacing be in synchrony with the earliest activation on the RV chamber. For example, in a fusion pacing configuration, a medical device delivers one or more fusion pacing pulses to a later-contracting left ventricle (LV) in order to pre-excite the LV and synchronize the depolarization of the LV with the depolarization of the earlier contracting right ventricle (RV). The ventricular activation of the LV may "fuse" (or "merge") with the ventricular activation of the RV that is attributable to intrinsic conduction of the heart. In this way, the intrinsic and pacing-induced excitation wave fronts may fuse together such that the depolarization of the LV is resynchronized with the depolarization of the RV.

Current therapy systems for delivering CRT typically include a right atrial lead extending into the right atrium (RA) of the patient's heart, a right ventricle lead that extends through the right atrium and into the right ventricle (RV), and a left ventricle lead that extends through the right, and into the coronary sinus to a region adjacent to the free wall of the left ventricle (LV) of the heart. What is needed is a method of verifying LV capture and and/or proper synchronization or fusion with other chambers of the heart during delivery of LV paving in a cardiac therapy device system having only a single-pass, left-sided, DDD lead that provides pacing and sensing of both the atria and the ventricles without requiring the introduction of a lead or an electrode into the right ventricle.

SUMMARY

The present disclosure is directed to a method and implantable medical device system for delivering LV pacing therapy that includes only a single pass coronary sinus lead. The single pass coronary sinus lead includes electrodes, which are spaced in a manner so that when the lead is positioned within the coronary sinus of the patient, the electrodes may be located near the left ventricle, and near the left atrium and/or the right atrium. In some examples, an electrode near the left ventricle may be located near the intra-ventricular septum.

In this way, the lead according to the present disclosure is designed to provide pacing and sensing of both the atria and the ventricles without requiring the introduction of a lead or an electrode into the right ventricle and may be referred to as a single-pass, left-sided DDD lead. The lead may be referred to as single-pass in that the single lead places electrodes proximate to both an atrium and a ventricle, and as left-sided in that the lead places electrodes proximate to the left ventricle, e.g., via the coronary sinus, rather than the right ventricle. The lead may also be referred to as single-pass coronary sinus lead.

According to one example of the present disclosure, a method for delivering a left ventricular (LV) cardiac pacing therapy to a patient, comprises: delivering the LV cardiac pacing therapy via an electrode of a plurality of electrodes; sensing far-field cardiac signals via one or more far-field sensing vectors formed between the plurality of electrodes; determining a beat morphology corresponding to the far-field cardiac signals sensed for each of the far-field sensing vectors to generate corresponding far-field beat morphologies; determining a beat morphology match between each of the far-field beat morphologies and an intrinsic beat morphology template; determining one of loss of LV capture, pseudo fusion and loss of synchrony in response to the determined beat morphology match; performing one of a loss of capture adjustment, a pseudo fusion adjustment, and a resynchronization adjustment in response to the determined one of loss of LV capture, pseudo fusion and loss of synchrony in response to the determined beat morphology match to generate an adjusted LV cardiac pacing therapy; and delivering the adjusted LV cardiac pacing therapy via an electrode of a plurality of electrodes.

Another example of the present disclosure includes an implantable medical device system for delivering a left ventricular (LV) cardiac pacing therapy to a patient, comprising: an implantable medical device housing; a single-pass coronary sinus lead capable of being electrically couple to the implantable medical device housing; a plurality of electrodes positioned along the single-pass coronary sinus lead to sense a far-field cardiac signal of the patient and deliver the LV cardiac pacing therapy; and a processor positioned within the implantable medical device housing and configured to sense far-field cardiac signals via one or more far-field sensing vectors formed between the plurality of electrodes, determine a beat morphology corresponding to the far-field cardiac signals sensed for each of the far-field sensing vectors to generate corresponding far-field beat morphologies, determine a beat morphology match between each of the far-field beat morphologies and an intrinsic beat morphology template, determine one of loss of LV capture, pseudo fusion and loss of synchrony in response to the determined beat morphology match, perform one of a loss of capture adjustment, a pseudo fusion adjustment, and a resynchronization adjustment in response to the determined one of loss of LV capture, pseudo fusion and loss of synchrony in response to the determined beat morphology match to generate an adjusted LV cardiac pacing therapy, and deliver the adjusted LV cardiac pacing therapy via an electrode of a plurality of electrodes.

Another example of the present disclosure includes a non-transitory computer readable medium storing instructions which cause an implantable medical device to perform a method, the method comprising: delivering the LV cardiac pacing therapy via an electrode of a plurality of electrodes; sensing far-field cardiac signals via one or more far-field sensing vectors formed between the plurality of electrodes; determining a beat morphology corresponding to the far-field cardiac signals sensed for each of the far-field sensing vectors to generate corresponding far-field beat morphologies; determining a beat morphology match between each of the far-field beat morphologies and an intrinsic beat morphology template; determining one of loss of LV capture, pseudo fusion and loss of synchrony in response to the determined beat morphology match; performing one of a loss of capture adjustment, a pseudo fusion adjustment, and a resynchronization adjustment in response to the determined one of loss of LV capture, pseudo fusion and loss of synchrony in response to the determined beat morphology match to generate an adjusted LV cardiac pacing therapy; and delivering the adjusted LV cardiac pacing therapy via an electrode of a plurality of electrodes.

DETAILED DESCRIPTION OF EXEMPLARY EMBODIMENTS

It will be apparent to a skilled artisan that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

In general, the present disclosure is directed to a method of verifying LV capture and and/or proper synchronization or fusion with other chambers of the heart during delivery of cardiac resynchronization pacing therapy in a cardiac therapy device system having only a single-pass, left-sided, DDD lead that provides pacing and sensing of both the atria and the ventricles without requiring the introduction of a lead or an electrode into the right ventricle. The lead may be referred to as single-pass in that the single lead places electrodes proximate to both an atrium and a ventricle, and as left-sided in that the lead places electrodes proximate to the left ventricle, e.g., via the coronary sinus, rather than the right ventricle.

For example, the cardiac therapy device system may include a housing or can and a single lead that is capable of providing left ventricular LV DDD pacing electrically coupled to the housing. The lead of the present disclosure may include four electrodes, which are spaced in a manner so that when the lead is positioned within the coronary sinus of the patient, the electrodes may be located near the left ventricle, and near the left atrium and/or the right atrium. In some examples, an electrode near the left ventricle may be located near the intra-ventricular septum. In other example, more than four electrodes, or less than 4 electrodes may be utilized.

Figure 1:
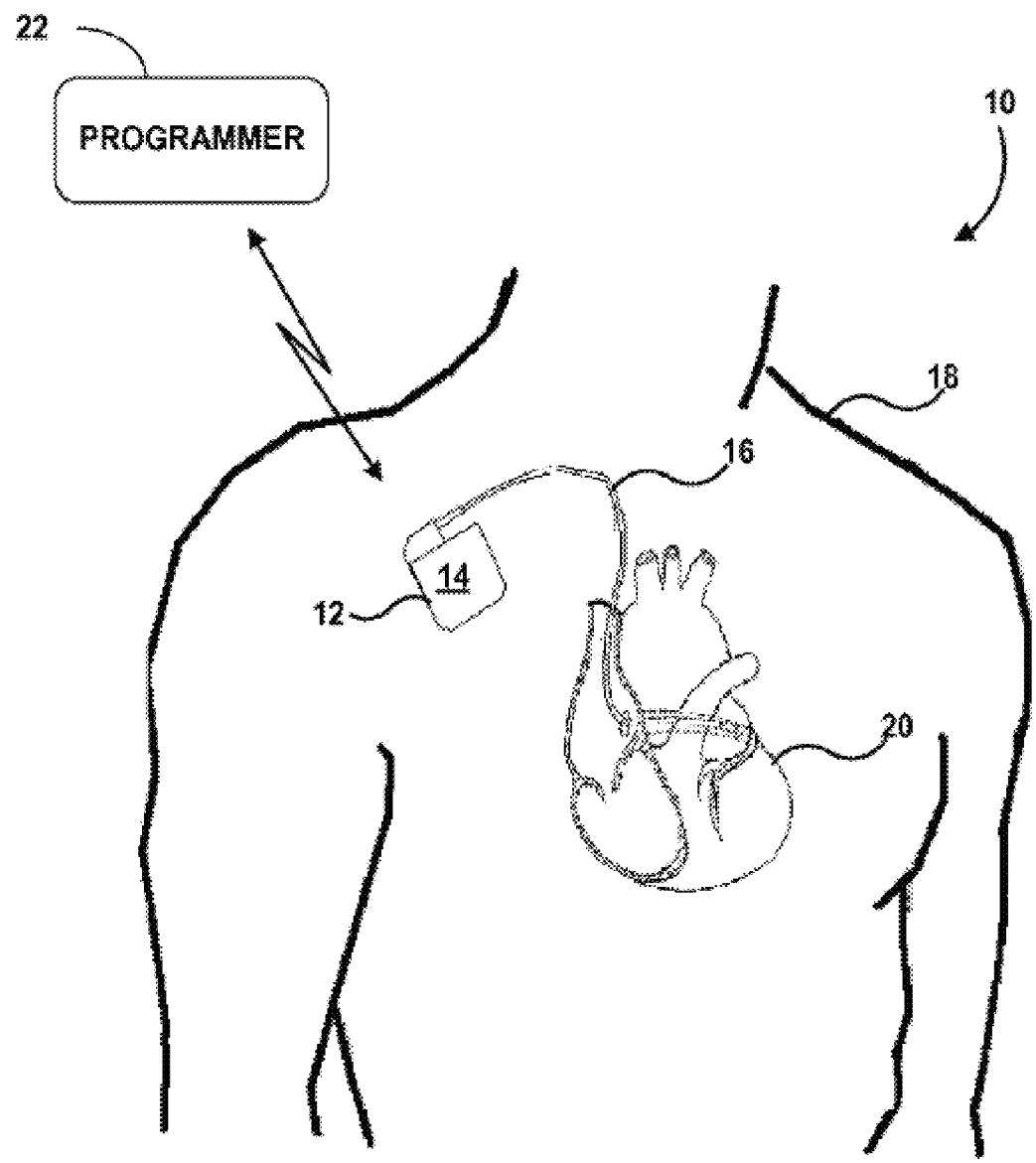
FIG. 1 is a conceptual diagram illustrating an example cardiac therapy device system for delivering pacing stimuli to a patient's heart in accordance with the present disclosure.

FIG. 1 is a conceptual diagram illustrating an example cardiac therapy device system for delivering pacing stimuli to a patient's heart in accordance with the present disclosure. As illustrated in FIG. 1, in one example, an implantable cardiac therapy device system 10 may include an implantable medical device (IMD) 12 and an implantable medical lead 16 electrically coupled to the IMD 12. In the example shown in FIG. 1, system 10 is implanted within a patient 18 to deliver electrical stimulation therapy to the heart 20 of patient 18. Patient 18 ordinarily, but not necessarily, will be a human patient.

In the example shown in FIG. 1, IMD 12 is a cardiac pacemaker, cardioverter, defibrillator, or pacemaker-cardioverter-defibrillator (PCD) that generates therapeutic electrical stimulation for pacing, cardioversion or defibrillation, which may take the form of pulses, e.g., about 1 to about 5 volt pacing pulses at a rate of about 50 to about 150 pulses per minute, or infrequent cardioversion/defibrillation stimuli of about 100 to about 800 volts. Lead 16 includes four electrodes that are each positioned within (e.g., intravascularly) heart 20 in order to deliver the therapeutic electrical stimulation from IMD 12 to the heart 20.

In the illustrated example, a distal end of lead 16 is positioned proximate to the left ventricle (LV) of patient 18, and more particularly, within the coronary sinus or a coronary vein accessed via the coronary sinus. In the illustrated example, lead 16 is configured for intravenous introduction into the heart 20. For example, lead 16 may have a lead body diameter between about 1 and about 3 millimeter. When lead 16 is positioned within the coronary sinus or coronary vein, the four electrodes (not shown in FIG. 1) may be positioned so that the two most proximal electrodes are positioned within or near the right atrium (RA) in close proximity to the AV node. In some examples, one electrode may be in the RA and one electrode may be within the coronary sinus. The third electrode may be located in the great cardiac vein and the fourth, and most distal, electrode may be located in one of the tributaries of the great coronary vein. For example, the fourth electrode may be located in the lateral coronary vein, the anterior coronary vein, or the anterior-lateral coronary vein. As described in further detail below, this configuration of electrodes allows for atrial sensing and pacing as well as ventricular sensing and pacing, as needed, using a single lead. Housing 14 of IMD 12 may be used as an anode in some examples.

To facilitate passage down narrow vessels, the electrodes of lead 16 are nearly the same diameter as the lead body, usually a fraction of a millimeter thicker to make sure they contact the vessel wall. Likewise, the helix fixation member 32 (FIG. 2) may also be slightly thicker than, e.g., a fraction of a millimeter thicker than, the lead body. Electrodes are typically about 0.2 to about 0.5 cm long. The whole lead is about 50 to about 100 cm in length, depending on the size of the patient.

As illustrated in FIG. 1, system 10 may also include a programmer 22, which may be a handheld device, portable computer, or workstation that provides a user interface to a clinician or other user. The clinician may interact with the user interface to program stimulation and sensing parameters for IMD 12, which may include, as examples, the electrodes of lead 16 which are activated for providing stimulation versus sensing, as well as selection from among different pacing modes, rate-response modes, inter-chamber intervals, arrhythmia detection algorithms, arrhythmia termination therapy progressions.

Programmer 22 supports telemetry (e.g., radio frequency telemetry) with IMD 12 to download stimulation parameters and, optionally, upload operational or physiological data stored by IMD 12. In this manner, the clinician may periodically interrogate IMD 12 to evaluate efficacy and, if necessary modify the operational parameters of the IMD. IMD 12 and programmer 22 may communicate via wireless communication as shown in FIG. 1. Programmer 22 may, for example, communicate via wireless communication with IMD 12 using RF telemetry techniques known in the art.

In some examples, at least one of the electrodes of lead 16 may function as a sensor that senses a physiological parameter of patient 12, such as, but not limited to, electrogram (EGM) parameters, a heart rate, QRS width, or atrioventricular (AV) dissociation. Sense electrodes may be the same electrodes used for delivery of electrical stimulation to patient 18, or different electrodes.

Figure 2:
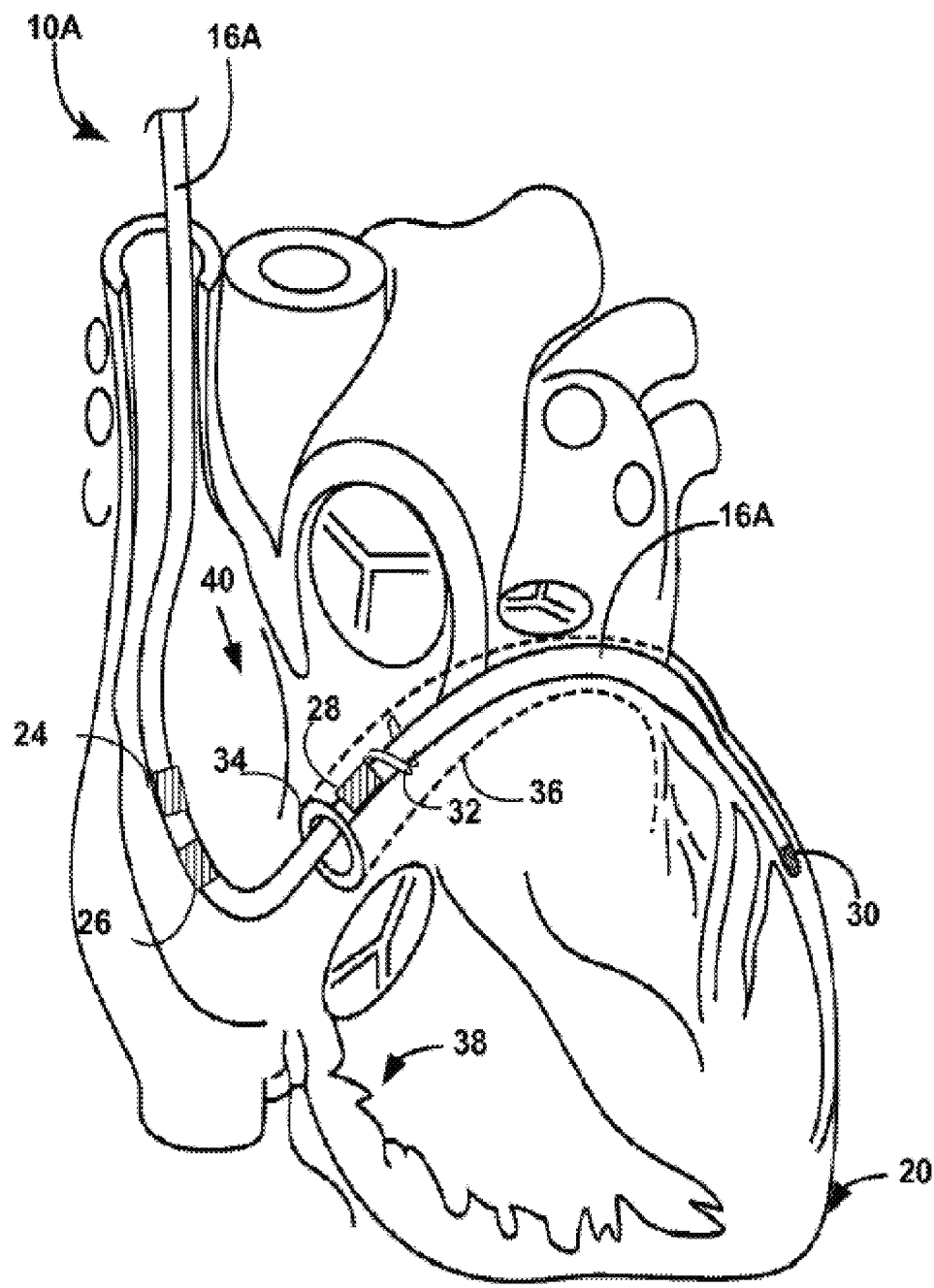
FIG. 2 is a conceptual diagram illustrating an example configuration of a lead of a cardiac therapy device system for delivering a pacing therapy to a patient's heart, in accordance with the present disclosure.

FIG. 2 is a conceptual diagram illustrating an example configuration of a lead of a cardiac therapy device system for delivering a pacing therapy to a patient's heart, in accordance with the present disclosure. As illustrated in FIG. 2, a lead 16A of a cardiac therapy device system 10A may include electrodes 24, 26, 28 and 30, along with a helix fixation member 32. In some examples, helix fixation member 32 may also be an electrode 28, e.g., helix fixation member 32 is conductive and acts as, or as part of, electrode 28. Lead 16A may be anchored to the wall of the coronary sinus 36, near the ostium 34 via helix fixation member 32. Lead 16A may be anchored by turning the lead clockwise to embed the helix fixation member 32 into the wall of the coronary sinus 36 when the electrodes are situated as desired within the heart 20.

As illustrated in FIG. 2, the electrodes of lead 16 are spaced so that electrodes 24 and 26 are located in RA 40. In some examples, electrodes 24 and 26 are floating electrodes within RA 40, e.g., do not necessarily contact the tissue of RA 40. For example, electrodes 24 and 26 may be floating atrial sense electrodes that function in a manner similar to floating sense electrodes in a conventional VDD lead. In some examples, electrodes 24 and 26 are located near the heart septum. In the example of FIG. 2, electrode 28 is located within coronary sinus 36, and electrode 30 is located at the distal end of lead 16, within one of the tributary veins of the great coronary vein. For example, electrode 30 may be located in the lateral coronary vein, the anterior coronary vein, or the anterior-lateral coronary vein. The tributary vein is selected so that electrode 30 is roughly adjacent the left ventricle (LV) and not as near the right ventricle (RV) apex. Electrodes 24 and 26 may be located less than approximately 1 cm apart. In some examples, electrodes 24 and 26 may be less than approximately 0.5 cm apart. The close spacing of atrial electrodes 24 and 26 may help to avoid R-wave over sensing, including far-field R-wave oversensing. In addition, the location of electrodes may aide in detecting the occurrence of an A-V block. In some examples, either of electrodes 24 and 26 may used in a unipolar configuration with an electrode formed on or by housing 14 to sense atrial activity. In some examples, electrode 28 may serve as an atrial pace cathode, with the housing 14 of IMD 12 functioning as the atrial pace anode. Electrode 28 may also serve as the ventricular sense-anode while electrode 30 may serves as the ventricular sense-cathode. The housing 14 may also function as an anode when electrode 30 delivers stimulation to LV 40.

Figure 3:
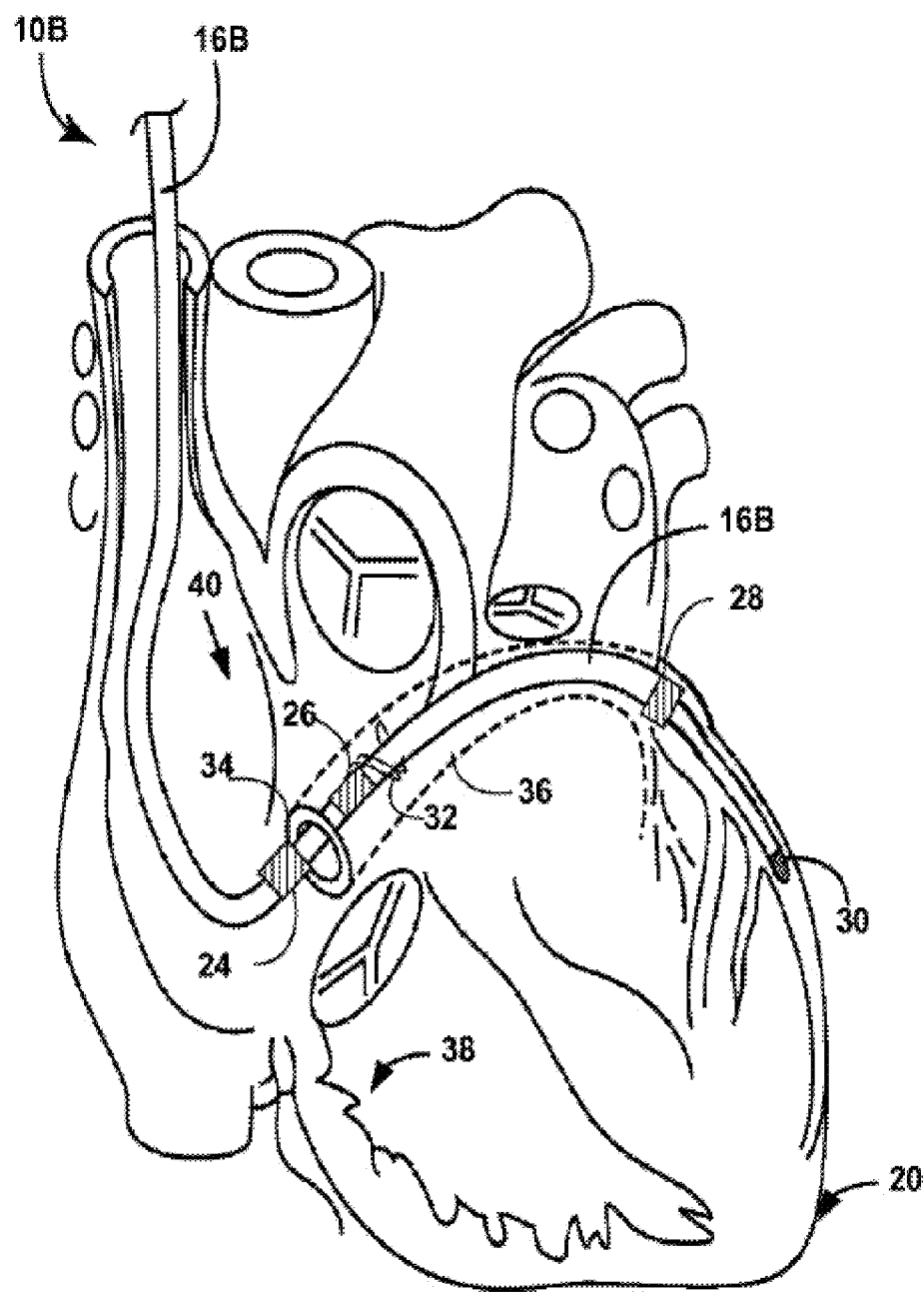
FIG. 3 is a conceptual diagram illustrating an example configuration of a lead of a cardiac therapy device system for delivering a pacing therapy to a patient's heart, in accordance with the present disclosure.

FIG. 3 is a conceptual diagram illustrating an example configuration of a lead of a cardiac therapy device system for delivering a pacing therapy to a patient's heart, in accordance with the present disclosure. As illustrated in FIG. 3, a lead 16B of an implantable cardiac therapy device system 10B may include electrodes 24, 26, 28 and 30, along with a helix fixation member 32, which may act as or be electrically coupled to electrode 26. Lead 16B may be anchored to the wall of the coronary sinus 36, near ostium 34 via helix fixation member 32. Lead 16B may be anchored by turning the lead clockwise to embed the helix fixation member 32 into the wall of the coronary sinus 36 when the electrodes are situated as desired within the heart. As illustrated in FIG. 3, the electrodes of lead 16 are spaced so that electrode 24 is located within RA 40, electrode 26 is located proximate to coronary sinus ostium 34, electrode 28 is located in the great cardiac vein, near the left atrium, and electrode 30 is located at the distal end of lead 16, within one of the tributary veins of the great coronary vein. For example, electrode 30 may be located in the lateral coronary vein, the anterior coronary vein, or the anterior-lateral coronary vein. The tributary vein is selected so that electrode 30 is roughly adjacent the left ventricle (LV) and not as near the right ventricle (RV) apex.

Electrodes 24 and 26 may act as a bipolar pair to sense atrial activity. Electrodes 24 and 26 may be located less than approximately 1 cm apart. In some examples, electrodes 24 and 26 may be less than approximately 0.5 cm apart. The close spacing of atrial electrodes 24 and 26 may help to avoid R-wave over sensing, including far-field R-wave oversensing. In addition, the location of electrodes may aide in detecting the occurrence of an A-V block. In some examples, either of electrodes 24 and 26 may used in a unipolar configuration with an electrode formed on or by housing 14 to sense atrial activity.

In some examples, electrode 26 may serve as an atrial pace cathode, with the housing 14 of IMD 12 functioning as the atrial pace anode. Electrode 28 may serve as the ventricular sense-anode while electrode 30 may serves as the ventricular sense-cathode, or either of electrodes 28 and 30 may be used in a unipolar configurations to sense electrical activity of the ventricles. Furthermore, electrodes 28 and 30 may be used to deliver bipolar pacing or other stimulation to LV 40, or either or both of electrodes 28 and 30 may be used in a unipolar configuration with an electrode of housing 14 to deliver unipolar stimulation. The housing 14 may function as an anode when electrodes 28 or 30 stimulate. In some examples, both of electrodes 28 and 30 may be used in a unipolar configuration to deliver sequential pacing to the ventricles. For example, electrode 28 may provide a first pacing pulse. A delay of approximately 10 milliseconds may be programmed between the pacing pulse from electrode 28 and a second pacing pulse from electrode 30. During delay electrode 30 is in sensing mode. If electrode 30 senses that the pulse from electrode 28 was successful in capturing the heart, then the pacing pulse from electrode 30 is inhibited. However, if the pacing pulse from electrode 28 does not result in capture, then electrode 30 provides the second pacing pulse.

Figure 4:
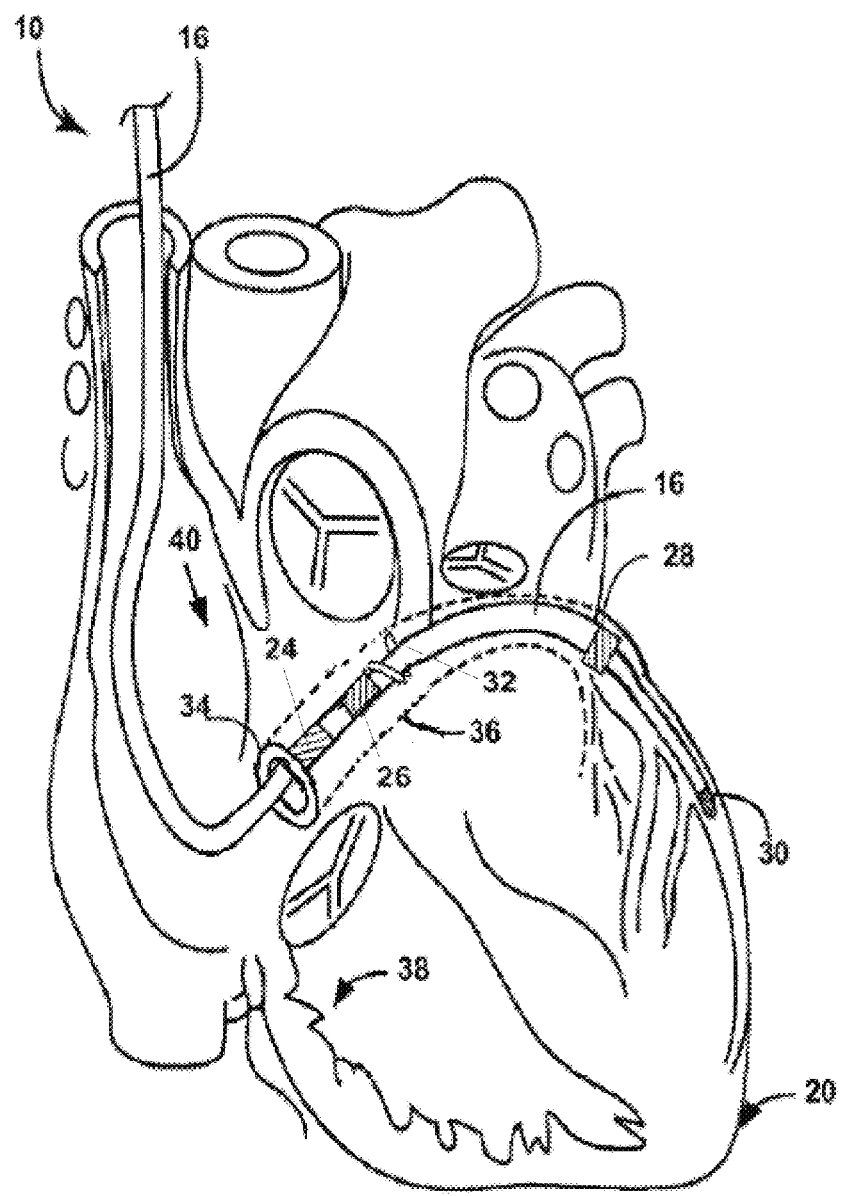
FIG. 4 is a conceptual diagram illustrating an example configuration of a lead of a cardiac therapy device system for delivering a pacing therapy to a patient's heart, in accordance with the present disclosure.

FIG. 4 is a conceptual diagram illustrating an example configuration of a lead of a cardiac therapy device system for delivering a pacing therapy to a patient's heart, in accordance with the present disclosure. As illustrated in FIG. 4, a lead 16C of an implantable cardiac therapy device system 10B may include electrodes 24, 26, 28 and 30, along with a helix fixation member 32, which may act as or be electrically coupled to electrode 26. Lead 16C may be anchored to the wall of the coronary sinus 36, near ostium 34 via helix fixation member 32. Lead 16C may be anchored by turning the lead 16C clockwise to embed the helix fixation member 32 into the wall of the coronary sinus 36 when the electrodes are situated as desired within the heart 20. As illustrated in FIG. 4, the electrodes of lead 16 are spaced so that electrode 24 is positioned with the coronary sinus 36 distally and in close proximity to the coronary sinus ostium 34, electrode 26 is located within the coronary sinus 36 distally from and in close proximity to electrode 24, electrode 28 is located in the great cardiac vein, near the left atrium, and electrode 30 is located at the distal end of lead 16, within one of the tributary veins of the great coronary vein. For example, electrode 30 may be located in the lateral coronary vein, the anterior coronary vein, or the anterior-lateral coronary vein. The tributary vein is selected so that electrode 30 is roughly adjacent the left ventricle (LV) and not as near the right ventricle (RV) apex.

As described above, electrodes 24 and 26 may act as a bipolar pair to sense atrial activity. Electrodes 24 and 26 may be located less than approximately 1 cm apart. In some examples, electrodes 24 and 26 may be less than approximately 0.5 cm apart. The close spacing of atrial electrodes 24 and 26 may help to avoid R-wave over sensing, including far-field R-wave oversensing. In addition, the location of electrodes may aide in detecting the occurrence of an A-V block. In some examples, either of electrodes 24 and 26 may used in a unipolar configuration with an electrode formed on or by housing 14 to sense atrial activity.

In some examples, electrode 26 may serve as an atrial pace cathode, with the housing 14 of IMD 12 functioning as the atrial pace anode. Electrode 28 may serve as the ventricular sense-anode while electrode 30 may serves as the ventricular sense-cathode, or either of electrodes 28 and 30 may be used in a unipolar configurations to sense electrical activity of the ventricles. Furthermore, electrodes 28 and 30 may be used to deliver bipolar pacing or other stimulation to LV 40, or either or both of electrodes 28 and 30 may be used in a unipolar configuration with an electrode of housing 14 to deliver unipolar stimulation. The housing 14 may function as an anode when electrodes 28 or 30 stimulate. In some examples, both of electrodes 28 and 30 may be used in a unipolar configuration to deliver sequential pacing to the ventricles. For example, electrode 28 may provide a first pacing pulse. A delay of approximately 10 milliseconds may be programmed between the pacing pulse from electrode 28 and a second pacing pulse from electrode 30. During delay electrode 30 is in sensing mode. If electrode 30 senses that the pulse from electrode 28 was successful in capturing the heart, then the pacing pulse from electrode 30 is inhibited. However, if the pacing pulse from electrode 28 does not result in capture, then electrode 30 provides the second pacing pulse.

Figure 5:
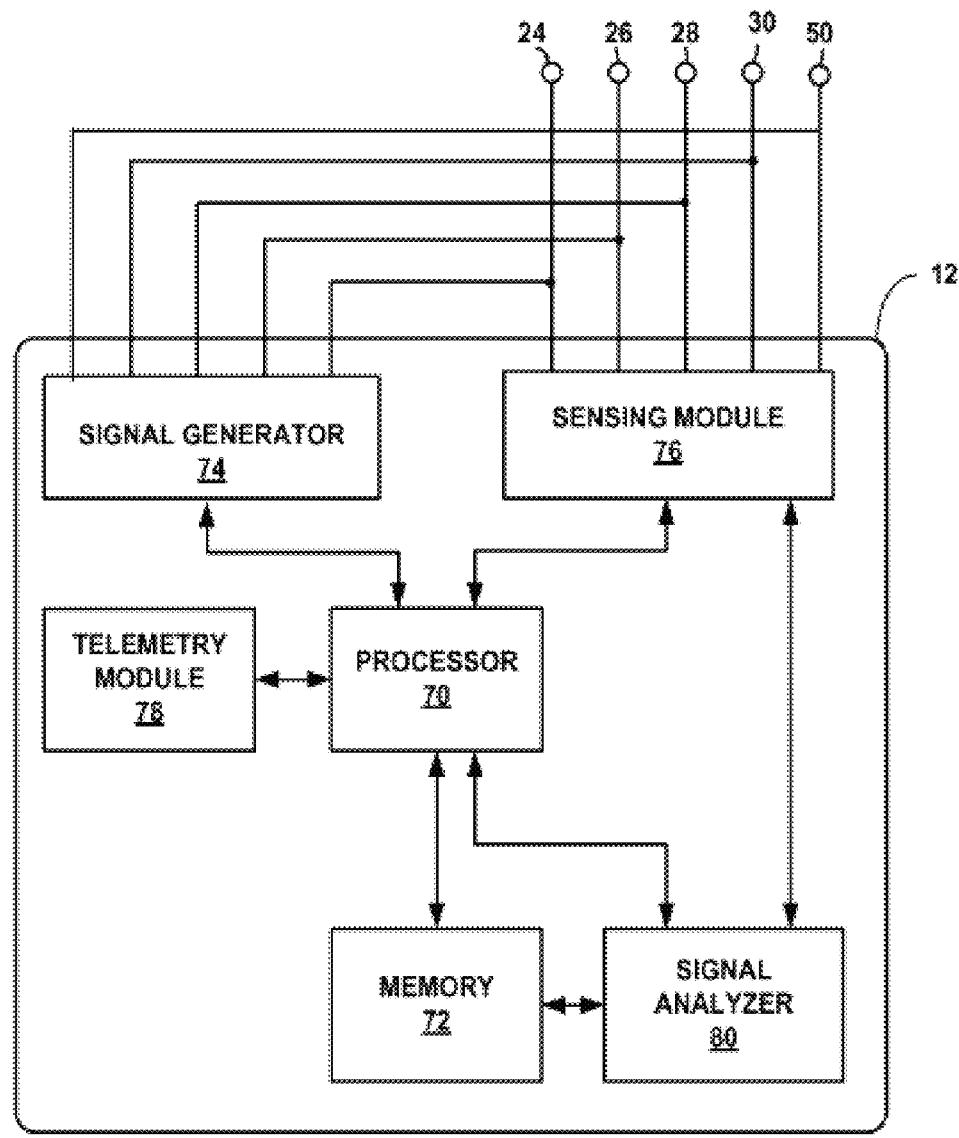
FIG. 5 is a functional block diagram of an implantable cardiac therapy device system for delivering a pacing therapy, in accordance with the present disclosure.

FIG. 5 is a functional block diagram of an implantable cardiac therapy device system for delivering a pacing therapy, in accordance with the present disclosure. As illustrated in FIG. 5, according to an example of the present disclosure, the IMD 12 may include a processor 70, memory 72, signal generator 74, sensing module 76, telemetry module 78, and signal analyzer 80. Memory 72 may include computer-readable instructions that, when executed by processor 70, cause IMD 12 and processor 70 to perform various functions attributed to IMD 12 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 and sensing module 76 to sense cardiac activity and deliver stimulation therapy to heart 20 of patient 18 according to a selected one or more operational modes, programs or parameters, which may be stored in memory 72.

Signal generator 74 is configured to generate and deliver electrical stimulation therapy to patient 18. As illustrated in FIG. 5, signal generator 74 is electrically coupled to electrodes 24, 26, 28 and 30 of lead 16. Signal generator 74 is also connected to a housing electrode 50 on or integral with housing 14. For example, signal generator 74 may deliver pacing pulses, to heart 20 via at least two of electrodes 24, 26, 28, 30 and 50. In other examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 24, 26, 28, 30 and 50. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70 and/or signal analyzer 80. One or more other detection channels may provide the signals to an analog-to-digital converter, for conversion into a digital signal for processing or analysis by processor 70 or signal analyzer 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76, processor 70, or signal analyzer 80. Processor 70 may analyze the digitized version of signals from the wide band channel. Processor 70 may employ digital signal analysis techniques to characterize the digitized signals from the wide band channel to, for example, detect and classify the patient's heart rhythms. In other examples, the signal analyzer 80 employs digital signal analysis techniques to characterize the digitized signals from the wide band channel.

Processor 70 may detect and classify the patient's heart rhythm based on the cardiac electrical signals sensed by sensing module 76 employing any of the numerous signal processing methodologies known in the art. In other examples, sensing module 76 provides the cardiac electrical signals sensed directed to signal analyzer 80. In some examples, sensing module 76 provides the sensed cardiac electrical signals to both processor 70 and signal analyzer 80 for different signal processing. In various examples, processor 70 may maintain escape interval counters that may reset upon sensing of R-waves by sensing modules 76. The value of the count present in the escape interval counters when reset by sensed depolarizations may be used by processor 70 to measure the durations of R-R intervals, which are measurement that may be stored in memory 72 and may be used by cardiac signal analyzer 80. Processor 70 may use the count in the interval counters to detect a tachyarrhythmia, such as ventricular fibrillation or ventricular tachycardia. A portion of memory 72 may be configured as a plurality of recirculating buffers, capable of holding a series of measured intervals, which may be analyzed by processor 70 to determine whether the patient's heart 20 is presently exhibiting atrial or ventricular tachyarrhythmia.

Cardiac resynchronization therapy (CRT) may correct the symptoms of electrical dyssynchrony by providing pacing therapy through medical electrical leads to one or both ventricles or atria to encourage earlier activation of the left or right ventricles. By pacing the contraction of the ventricles, the ventricles may be controlled so that the ventricles contract in synchrony.

Cardiac resynchronization pacing devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. Delivering electrical stimuli that causes the ventricle to respond is commonly referred to as capturing a ventricle. For a variety of reasons, cardiac pacing systems may not achieve effective capture of a ventricle. For example, a pacing lead and/or electrode may not be placed in an optimal location. Sensed atrioventricular delay (SAV), paced atrioventricular delay (PAV), right ventricular pre-excitation may also affect whether a ventricle is effectively captured. Exemplary reasons for ineffective capture include a sensed atrioventricular delay (SAV) that is too long, a paced atrioventricular delay (PAV) that is too long, and RV pre-excitation are typically addressed through adjusting delivery of the electrical stimuli to the ventricle. Other exemplary reasons for ineffective capture may include occurrence of atrial fibrillation (AF), a medical electrical lead placed in scar tissue, loss of capture due to lead dislodgement, atrial under sensing, a rate above an upper tracking rate, and the right and left ventricular leads are too close. Additionally, after the medical device has been implanted, migration or dislodgement of the pacing lead may occur, resulting in ineffective capture.

One specific form of CRT is known as fusion pacing, which typically involves left ventricle (LV) only pacing with an electrode on the LV medical electrical lead in coordination with the intrinsic right ventricle (RV) activation. Effective fusion requires, for example, that the timing of the LV pacing be in synchrony with the earliest activation on the RV chamber. For example, in a fusion pacing configuration, a medical device delivers one or more fusion pacing pulses to a later-contracting left ventricle (LV) in order to pre-excite the LV and synchronize the depolarization of the LV with the depolarization of the earlier contracting right ventricle (RV). The ventricular activation of the LV may "fuse" (or "merge") with the ventricular activation of the RV that is attributable to intrinsic conduction of the heart. In this way, the intrinsic and pacing-induced excitation wave fronts may fuse together such that the depolarization of the LV is resynchronized with the depolarization of the RV. In some cases, the delivered LV pacing therapy may result what is known as pseudo fusion, in which the timing of the ventricular output pulse results in a ventricular pacing pulse falling into the absolute refractory period of the intrinsic, conducted R-wave, resulting in a pseudo fusion beat.

As described in detail below, the present disclosure provides a method of verifying LV capture and and/or proper synchronization or fusion with other chambers of the heart during delivery of LV paving in a cardiac therapy device system having only a single-pass, left-sided, DDD lead that provides pacing and sensing of both the atria and the ventricles without requiring the introduction of a lead or an electrode into the right ventricle. For example, the present disclosure is directed to a cardiac therapy device system having only a single-pass, left-sided, DDD lead that utilizes far-field electrogram morphology to a) verify LV capture and b) verify proper synchronization with the other chambers of the heart, more specifically fusion with intrinsic conduction. If the morphology analysis suggests loss of LV capture the device increases the pacing output or switches stimulation to a different pacing electrode pair/vector. On the other hand, if the morphology analysis suggests loss of synchronization, the device adjusts pacing timing. By only using a single-pass, left-sided, DDD lead, the cardiac therapy device system of the present disclosure reduces the risk of the occurrence of complications due to there being less device hardware being introduced within the patient's body compared to current therapy systems for delivering CRT that typically include a right atrial lead, a right ventricle lead, and a left ventricle lead.

Figure 6:
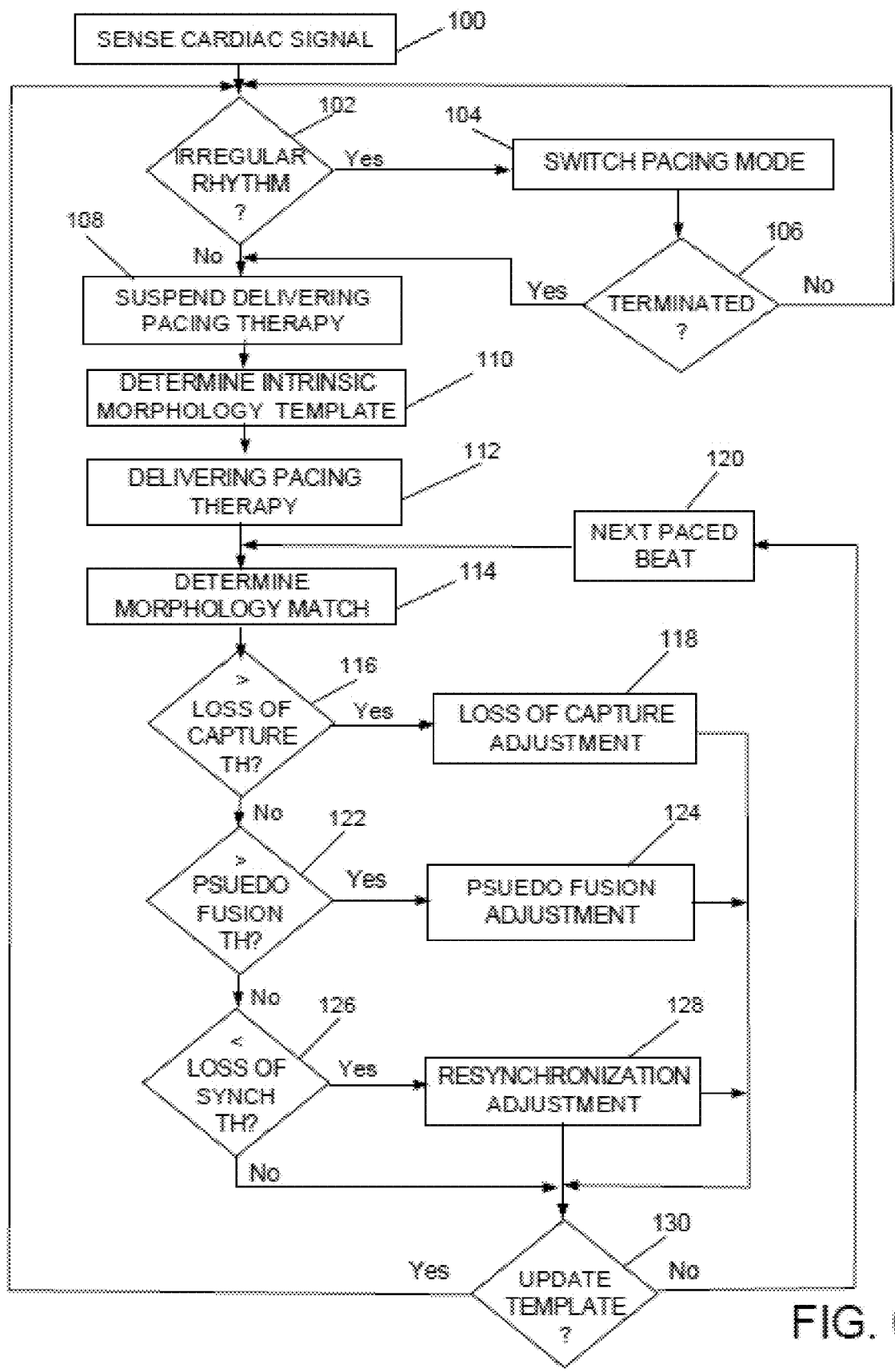
FIG. 6 is a flowchart of a method of delivering a pacing therapy in a cardiac therapy device system in accordance with the present disclosure.

FIG. 6 is a flowchart of a method of delivering a pacing therapy in a cardiac therapy device system in accordance with the present disclosure. As illustrated in FIG. 6, according to an example of the present disclosure, during delivery of cardiac resynchronization therapy, the processor 70 senses cardiac signals via any one or combination of electrodes 24, 26, 28, 30 and 50, Block 100, and determines whether an irregular heart rhythm is occurring, Block 102, based on or in response to the sensed cardiac signal(s). For example, the device 12 may sense far-field cardiac signals, Block 104, from three sensing vectors, such as the far-field sensing vector formed between electrode 24 and the electrode formed by the housing 14 of the device 12, the far-field sensing vector formed between electrode 30 and the electrode formed by the housing 14 of the device 12, and the far-field sensing vector formed between electrode 24 and electrode 30 of the lead 16.

In one example, if an irregular rhythm is determined to be occurring, Yes in Block 102, the processor 70 may switch the pacing mode associated with delivery of the cardiac resynchronization therapy by the device 12. For example, the processor 70 may switch from an LV DDD pacing mode delivered during CRT pacing to an asynchronous VVI pacing mode, Block 104, and may subsequently switch back to the LV DDD pacing mode once the irregular rhythm is terminated, Yes in Block 106. In this way, once the processor 70 determines the sensed cardiac signal is associated with normal or regular cardiac rhythm, the processor 70 suspends or delays delivery of the CRT pacing, Block 108, in order to evaluate intrinsic, non-paced, electrical conduction for use in generating or determining an intrinsic beat morphology template, Block 110, from the sensed intrinsic cardiac signal.

Once the intrinsic beat morphology template is generated, Block 110, the processor 70 resumes delivery of the CRT pacing by the device 12, Block 112, and senses paced, or non-intrinsic signals, via one or more far-field sensing vectors formed between any combination of electrodes 24, 26, 28, 30 and 50. For example, the processor 70 may continue to sense cardiac signals from the far-field sensing vectors formed between electrode 24 and the electrode formed by the housing 14 of the device 12, between electrode 30 and the electrode formed by the housing 14 of the device 12, and between electrode 24 and electrode 30 of the lead 16. The processor 70 determines, on a beat-by-beat basis, a beat morphology for the cardiac signal sensed for each far-field sensing vector to generate corresponding far-field cardiac signal beat morphologies. The processor 70 compares each of the generated far-field cardiac signal morphologies to the intrinsic beat morphology template and determines a beat morphology match between the far-field beat morphologies and the determined intrinsic beat morphology template for each of the generated far-field cardiac signal beat morphologies, Block 114. For example, the processor may generate the intrinsic beat morphology template based on the morphology of an intrinsic R-wave of the sensed cardiac signal, and therefore determine the beat morphology match, Block 114, by comparing an evoked response, or R-wave, of the cardiac signal(s) sensed via each of the far-field sensing vector(s) to the intrinsic beat morphology temple, i.e., intrinsic R-wave.

According to one example, the processor 70 may utilize any known waveform template acquisition and matching algorithm to generate the intrinsic beat morphology template in Block 110, and to determine the beat morphology match score, Block 114. For example, a wavelet method for template acquisition and ECG signal analysis, as generally described in U.S. Pat. No. 6,393,316 (Gillberg, et al.) and U.S. Pat. No. 7,062,315 (Koyrakh, et al.), both of which patents are incorporated herein by reference in their entirety, may be utilized. It is understood that while the wavelet method for template generation and beat morphology matching is described herein, other waveform template matching algorithms known in the art such as correlation, area of difference, etc., may also be utilized.

The intrinsic beat morphology template may be generated by digitizing and averaging a predetermined number of consecutively or non-consecutively sensed far-field cardiac cycles, e.g. 3 to 8 cardiac cycles. It is recognized that the template generation may be postponed when the ECG signal is determined to be noisy or the heart rate is not determined to be normal sinus rhythm, i.e. an arrhythmia is being detected. The determination of the beat morphology match score may involve comparisons of peak amplitudes, zero-crossing, signal widths, signal slopes or any other features of the ECG signal. Comparisons may further involve various waveform analysis methods such as Correlation Waveform Analysis (CWA), Area of Difference Analysis (AD), wavelet transform analysis, or other methods.

Once a beat morphology match has been determined for the evoked response from the far-field sensing vectors, the processor 70 may determine whether loss of LV capture is indicated by determining whether the beat morphology match score, Block 114, is greater than a loss of capture threshold, Block 116. If the determined beat morphology match score is greater than the loss of capture threshold, Yes in Block 116, loss of capture is indicated and therefore the processor 70 may make a loss of capture adjustment to the pacing therapy, Block 118.

For example, in order to perform the loss of capture adjustment, Block 118, the processor may increase the pacing output or switch to a different pacing electrode. In one example, the loss of capture threshold may be set as being a 90 percent beat morphology match so that if the match score between the paced beat morphology and the intrinsic beat morphology is determined to be greater than a 90% match, the beat morphology match between the paced beat morphology and the intrinsic beat morphology is determined to be very high, and therefore the current delivered pacing therapy is determined to result in non-capture or loss of capture.

After making the loss of capture adjustment, Block 118, the processor 70 determines whether a predetermined time period for updating the beat morphology template since the last update has expired, and therefore the beat morphology template is to be updated, Yes in Block 130. In one example, the predetermined time period may be 16 hours so that the intrinsic beat morphology template is updated every 16 hours. If the predetermined time period for updating the beat morphology template has not expired, No in Block 130, the process is then repeated for the evoked response associated with the next paced beat, Block 120. On the other hand, if the predetermined time period for updating the beat morphology template has expired, Yes in Block 130, indicating that the beat morphology template is to be updated, the processor 70 repeats the determination of the intrinsic beat morphology template, Block 110, from the sensed intrinsic cardiac signal, as described above, to generate an updated intrinsic beat morphology template.

If the determined beat morphology match between the paced beat morphology and the intrinsic beat morphology is not greater than the loss of capture threshold, No in Block 116, the processor 70 may determine whether pseudo fusion is indicated by determining whether the current determined beat morphology match, Block 114, is greater than a pseudo fusion threshold, Block 122. If the determined beat morphology match score is greater than the pseudo fusion threshold, Yes in Block 122, pseudo fusion is indicated and therefore the processor 70 makes a pseudo fusion adjustment to the pacing therapy, Block 124.

For example, in order to perform the pseudo fusion adjustment, Block 124, the processor 70 may shorten or decrease the AV delay associated with the currently delivered pacing therapy. In one example, the pseudo fusion threshold may be set as being an 80 percent beat morphology match, so that if the match score between the paced beat morphology and the intrinsic beat morphology is determined to be greater than an 80 percent match, but less than or equal to a 90 percent match, the beat morphology match between the paced beat morphology and the intrinsic beat morphology is determined to be high, and therefore pseudo fusion is suspected or indicated for the current delivered pacing therapy.

After making the pseudo fusion adjustment, Block 124, the processor 70 determines whether the predetermined time period for updating the beat morphology template since the last update has expired, and therefore the beat morphology template is to be updated, Block 130. If the predetermined time period for updating the beat morphology template has not expired, No in Block 130, the process is then repeated for the evoked response associated with the next paced beat, Block 120. On the other hand, if the predetermined time period for updating the beat morphology template has expired, Yes in Block 130, the processor 70 repeats the determination of the intrinsic beat morphology template, Block 110, from the sensed intrinsic cardiac signal, as described above, to generate an updated intrinsic beat morphology template.

If the determined beat morphology match scores are not greater than the pseudo fusion capture threshold, No in Block 122, the processor 70 may determine whether loss of synchrony is indicated by determining whether the current beat morphology match, Block 114, is less than a loss of synchrony threshold, Block 126. If the determined beat morphology match is less than the loss of synchrony threshold, Yes in Block 126, loss of synchrony is indicated and therefore the processor 70 may make a resynchronization adjustment to the pacing therapy, Block 128.

For example, in order to perform the resynchronization adjustment, Block 128, when the device 12 is operating in the LV DDD mode, the processor 70 may increase the AV delay associated with the delivered pacing therapy. In one example, the loss of synchrony threshold may be set as being a 20 percent beat morphology match, so that if the match score between the paced beat morphology and the intrinsic beat morphology is determined to be less than 20 percent, the beat morphology match between the paced beat morphology and the intrinsic beat morphology is determined to be low, therefore the current delivered pacing therapy is determined to result in there being a lack of LV-RV resynchronization, or in non-fused pacing, and loss of synchronization is suspected or indicated for the current delivered pacing therapy.

After making the resynchronization adjustment, Block 128, the processor 70 determines whether the predetermined time period for updating the beat morphology template since the last update has expired, and therefore the beat morphology template is to be updated, Block 130. If the predetermined time period for updating the beat morphology template has not expired, No in Block 130, the process is then repeated for the evoked response associated with the next paced beat, Block 120. On the other hand, if the predetermined time period for updating the beat morphology template has expired, Yes in Block 130, the processor 70 repeats the determination of the intrinsic beat morphology template, Block 110, from the sensed intrinsic cardiac signal, as described above, to generate an updated intrinsic beat morphology template.

According to one example of the present disclosure, if the current determined beat morphology match score is not greater than the loss of capture threshold, No in Block 116, is not greater than the pseudo fusion threshold, No in Block 122, and is not less than the loss of synchronization threshold, No in Block 126, and therefore neither loss of capture, pseudo fusion or loss of synchronization are indicated for the current paced beat, the processor 70 determines whether the predetermined time period for updating the beat morphology template since the last update has expired, and therefore the beat morphology template is to be updated, Block 130. If the predetermined period of time for updating the beat morphology template has not expired, No in Block 130, the process is then repeated for the evoked response associated with the next paced beat, Block 120. On the other hand, if the predetermined time period for updating the beat morphology template has expired, Yes in Block 130, the processor 70 repeats the determination of the intrinsic beat morphology template, Block 110, from the sensed intrinsic cardiac signal, as described above, to generate an updated intrinsic beat morphology template.

Figure 7:
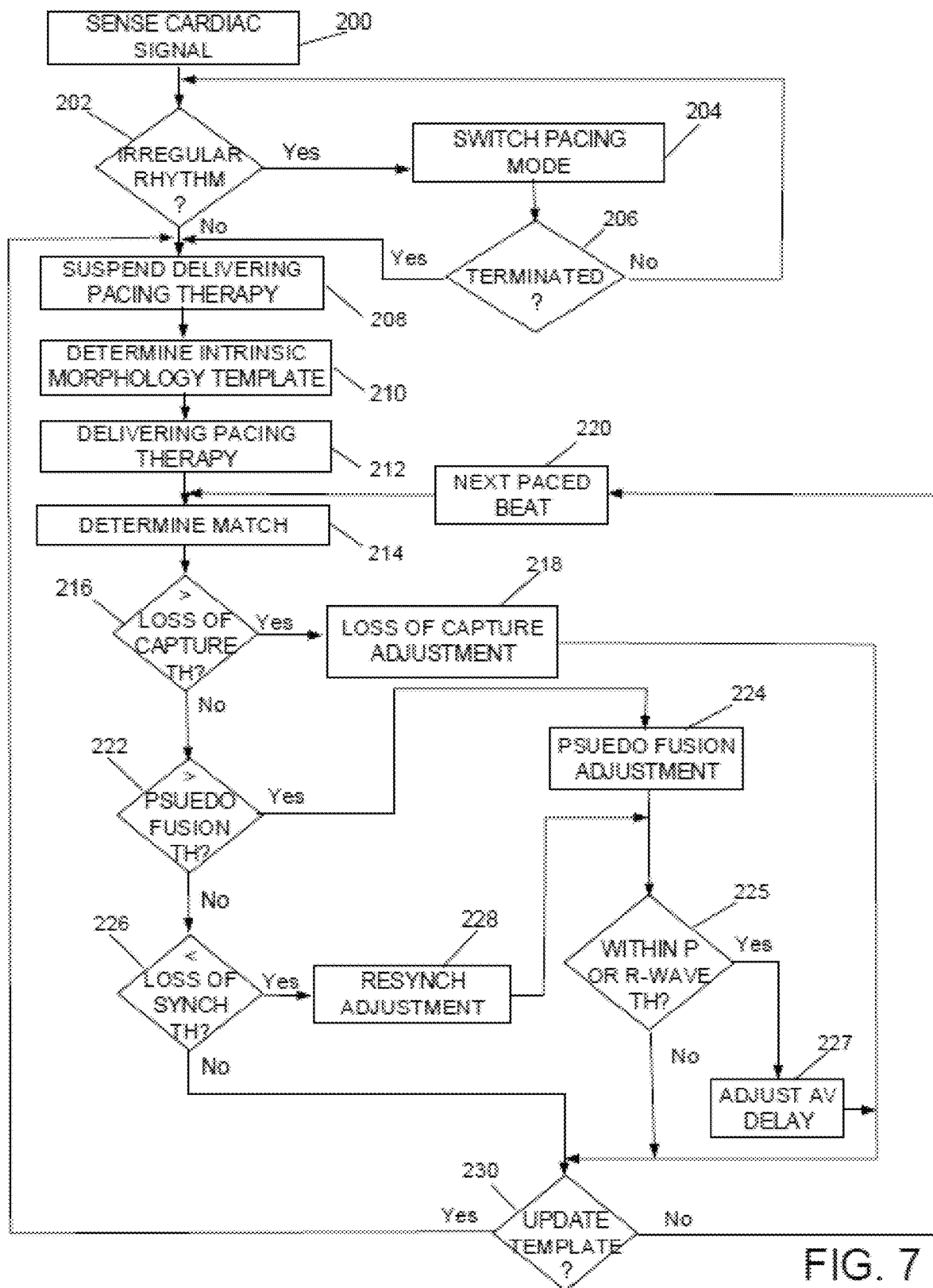
FIG. 7 is a flowchart of a method of delivering a pacing therapy in a cardiac therapy device system in accordance with the present disclosure.

FIG. 7 is a flowchart of a method of delivering a pacing therapy in a cardiac therapy device system in accordance with the present disclosure. As illustrated in FIG. 7, according to an example of the present disclosure, during delivery of cardiac resynchronization therapy, the processor 70 senses cardiac signals via any one or combination of electrodes 24, 26, 28, 30 and 50, Block 200, and determines whether an irregular heart rhythm is occurring, Block 202, based on or in response to the sensed cardiac signal(s). For example, the device 12 may sense far-field cardiac signals from three far-field sensing vectors, such as the far-field sensing vector formed between electrode 24 and the electrode formed by the housing 14 of the device 12, the far-field sensing vector formed between electrode 30 and the electrode formed by the housing 14 of the device 12, and the far-field sensing vector formed between electrode 24 and electrode 30 of the lead 16.

In one example, if an irregular rhythm is determined to be occurring, Yes in Block 202, the processor 70 may switch the pacing mode associated with delivery of the cardiac resynchronization therapy by the device 12. For example, the processor 70 may switch from an LV DDD pacing mode delivered during CRT pacing to an asynchronous VVI pacing mode, Block 104, and subsequently switch back to the LV DDD pacing mode once the irregular rhythm is terminated, Yes in Block 106. In this way, once the processor 70 determines the sensed cardiac signal is associated with normal or regular cardiac rhythm, the processor 70 suspends or delays delivery of the CRT pacing, Block 208, in order to evaluate non-paced, intrinsic electrical conduction for use in generating or determining an intrinsic beat morphology template, Block 210, from the sensed intrinsic cardiac signal.

Once the intrinsic beat morphology template is determined, Block 210, the processor 70 resumes delivery of the CRT pacing by the device 12, Block 212, and senses paced, or non-intrinsic signals, via one or more far-field sensing vectors formed between any combination of electrodes 24, 26, 28, 30 and 50, as described above in reference to FIG. 6. The processor 70 determines, on a beat-by-beat basis, a beat morphology associated with the cardiac signal sensed for each far-field sensing vector to generate corresponding far-field cardiac paced beat morphologies. The processor 70 compares each of the generated far-field cardiac paced beat morphologies to the intrinsic beat morphology template and determines a beat morphology match between the far-field signals and the determined intrinsic beat morphology template for each of the generated far-field cardiac paced beat morphologies, Block 214.

According to one example, the processor 70 may utilize any known waveform template acquisition and matching algorithm to generate the intrinsic beat morphology template in Block 210, and to determine the beat morphology match, Block 214, as described above in reference to FIG. 6. In one example, as described above, the processor 70 may generate the intrinsic beat morphology template based on the morphology of an intrinsic R-wave of the sensed cardiac signal, and therefore determine the beat morphology match, Block 214, by comparing an evoked response, or R-wave, of the cardiac signal(s) sensed via each of the far-field sensing vector(s) to the intrinsic beat morphology temple, i.e., intrinsic R-wave.

Once a beat morphology match, Block 214, has been determined for the evoked response from the far-field sensing vector or vectors, the processor 70 may determine whether loss of LV capture is indicated. For example, the processor 70 may determine whether the beat morphology match score, Block 214, is greater than a loss of capture threshold, Block 216. If the determined beat morphology match score is greater than the loss of capture threshold, Yes in Block 216, loss of capture is indicated. As result, the processor 70 may make a loss of capture adjustment to the pacing therapy, Block 218, to address the indicated loss of capture.

For example, in order to perform the loss of capture adjustment, Block 218, the processor may increase the pacing output or switch to a different pacing electrode. In one example, the loss of capture threshold may be set as being a 90 percent beat morphology match so that if the beat morphology match score between the paced beat morphology and the intrinsic beat morphology is determined to be greater than a 90% match, the beat morphology match between the paced beat morphology and the intrinsic beat morphology is determined to be very high, and therefore non-capture or loss of capture is suspected or indicated for the current delivered pacing therapy.

After making the loss of capture adjustment, Block 218, the processor 70 determines whether to update the intrinsic beat morphology template, Block 230. For example, updating of the template may be programmed to occur for a predetermined time period, such as 16 hours, so that the intrinsic beat morphology template is updated every 16 hours. If the predetermined time period for updating the beat morphology template has not expired, and therefore it is determined that the intrinsic beat morphology template is not to be updated, No in Block 230, the process is then repeated for the evoked response associated with the next paced beat, Block 220. On the other hand, if the predetermined time period for updating the beat morphology template has expired, indicating that the beat morphology template is to be updated, Yes in Block 230, the processor 70 repeats the determination of the intrinsic beat morphology template, Block 210, from the sensed intrinsic cardiac signal, as described above, to generate an updated intrinsic beat morphology template.

If the determined beat morphology match between the paced beat morphology and the intrinsic beat morphology is not greater than the loss of capture threshold, No in Block 216, the processor 70 may determine whether pseudo fusion is indicated. For example, the programmer 70 may determine whether the current determined beat morphology match, Block 214, is greater than a pseudo fusion threshold, Block 222. If the determined beat morphology match score is greater than the pseudo fusion threshold, Yes in Block 222, pseudo fusion is indicated. Therefore, the processor 70 may make a pseudo fusion adjustment to the pacing therapy, Block 224.

For example, in order to perform the pseudo fusion adjustment, Block 124, the processor 70 may shorten or decrease the AV delay associated with the currently delivered pacing therapy. In one example, the pseudo fusion threshold may be set as being an 80 percent beat morphology match, so that if the beat morphology match score between the paced beat morphology and the intrinsic beat morphology is determined to be greater than an 80 percent match, but less than or equal to a 90 percent match, the beat morphology match between the paced beat morphology and the intrinsic beat morphology is determined to be high, and therefore pseudo fusion is suspected or indicated for the current delivered pacing therapy.

The processor 70 may then determine whether delivery of pacing therapy adjusted according to the pseudo fusion adjustment will result in the pacing therapy being delivered either too close to the P-wave or too close to the R-wave. For example, the processor 70 may determine whether the pacing therapy is delivered either within a P-wave threshold or within an R-wave threshold, Block 225. In one example, the P-wave threshold may be set as being a 30 ms window subsequent to the end of a P-wave of the corresponding cardiac signal and the R-wave threshold may be set as being a 30-40 ms window prior to the R-wave of the cardiac signal. If the adjustment to the delivered pacing therapy would result in the pacing therapy being delivered either within the P-wave or within the R-wave threshold, Yes in Block 225, the processor 70 may adjust the AV delay, Block 227.

Once the adjustment to the AV delay is made, Block 227, or if the adjustment to the delivered pacing therapy would not result in the adjusted pacing therapy being delivered within the P-wave or the R-wave threshold, No in Block 225, the processor 70 may determine whether to update the intrinsic beat morphology template, Block 230, as described above. If the predetermined period of time for updating the beat morphology template has not expired, and therefore it is determined that the intrinsic beat morphology template is not to be updated, No in Block 230, the process is then repeated for the evoked response associated with the next paced beat, Block 220. On the other hand, if the predetermined time period for updating the beat morphology template has expired, indicating that the beat morphology template is to be updated, Yes in Block 230, the processor 70 repeats the determination of the intrinsic beat morphology template, Block 210, from the sensed intrinsic cardiac signal, as described above, to generate an updated intrinsic beat morphology template.

If the determined beat morphology match scores are not greater than the pseudo fusion threshold, No in Block 222, the processor 70 may determine whether loss of synchrony is indicated. For example, the processor 70 may determine whether the current beat morphology match, Block 214, is less than a loss of synchrony threshold, Block 226. If the determined beat morphology match is less than the loss of synchrony threshold, Yes in Block 226, loss of synchrony is indicated and therefore the processor 70 may make a loss of synchrony adjustment to the pacing therapy, Block 228.

For example, in order to perform the loss of synchrony adjustment, Block 228, when the device 12 is operating in the LV DDD mode, the processor 70 may increase the AV delay associated with the delivered pacing therapy. In one example, the loss of synchrony threshold of Block 226 may be set as being a 20 percent beat morphology match so that if the bet morphology match score between the paced beat morphology and the intrinsic beat morphology is determined to be low and therefore loss of synchrony or non-fused pacing is indicated for the current delivered pacing therapy.

The processor 70 may then determine whether delivery of pacing therapy adjusted according to the resynchronization adjustment, Block 228, will result in the pacing therapy being delivered either too close to the P-wave or too close to the R-wave. For example, the processor 70 may determine whether the pacing therapy is delivered either within a P-wave threshold or within an R-wave threshold, Block 225, as described above. If the adjustment to the delivered pacing therapy would result in the pacing therapy being delivered either within the P-wave or within the R-wave threshold, Yes in Block 225, the processor 70 may adjust the AV delay, Block 227.

Once the adjustment to the AV delay is made, Block 227, or if the adjustment to the delivered pacing therapy would not result in the adjusted pacing therapy being delivered within the P-wave or the R-wave threshold, No in Block 225, the processor 70 may determine whether to update the intrinsic beat morphology template, Block 230, as described above. If the predetermined time period for updating the beat morphology template has not expired, and therefore it is determined that the intrinsic beat morphology template is not to be updated, No in Block 230, the process is then repeated for the evoked response associated with the next paced beat, Block 220. On the other hand, if the predetermined time period for updating the beat morphology template has expired, indicating that the beat morphology template is to be updated, Yes in Block 230, the processor 70 repeats the determination of the intrinsic beat morphology template, Block 210, from the sensed intrinsic cardiac signal, as described above, to generate an updated intrinsic beat morphology template.

According to one example of the present disclosure, if the current determined beat morphology match score is not greater than the loss of capture threshold, No in Block 216, is not greater than the pseudo fusion threshold, No in Block 222, and is not less than the loss of synchronization threshold, No in Block 226, and therefore neither loss of capture, pseudo fusion or loss of synchronization are indicated for the current paced beat, the processor 70 may determine whether to update the intrinsic beat morphology template, Block 230, as described above. If the predetermined period of time for updating the beat morphology template has not expired, and therefore it is determined that the intrinsic beat morphology template is not to be updated, No in Block 230, the process is then repeated for the evoked response associated with the next paced beat, Block 220. On the other hand, if the predetermined period of time for updating the beat morphology template has expired, indicating that the beat morphology template is to be updated, Yes in Block 230, the processor 70 repeats the determination of the intrinsic beat morphology template, Block 210, from the sensed intrinsic cardiac signal, as described above, to generate an updated intrinsic beat morphology template.

In an example in which more than one far-field sensor vector is utilized, such as the far-field sensing vector formed between electrode 24 and the electrode formed by the housing 14 of the device 12, the far-field sensing vector formed between electrode 30 and the electrode formed by the housing 14 of the device 12, and the far-field sensing vector formed between electrode 24 and electrode 30 of the lead 16, the determination of the beat morphology match, Block 114, 214, includes comparing a paced beat morphology for each far-field sensing vectors to the intrinsic beat morphology template. The processor 70 may then utilize the paced beat morphology that differs most from the intrinsic beat morphology template to determine whether loss of capture, pseudo fusion or loss of synchronization are indicated for the current paced beat. Therefore, in an example where the paced beat morphology match determined for the far-field sensing vector formed between electrode 24 and the electrode formed by the housing 14 of the device 12 is 91 percent, the paced beat morphology match determined for the far-field sensing vector formed between electrode 30 and the electrode formed by the housing 14 of the device 12 is 85 percent, and the paced beat morphology match determined for the far-field sensing vector formed between electrode 24 and electrode 30 of the lead 16 is 43 percent, the processor 70 would use the paced beat morphology match score of 43 percent in determining whether loss of capture, pseudo fusion or loss of synchronization are indicated for the current paced beat, as described above. In another example, the processor 70 may take the average of the determined paced beat morphology match for each far-field sensing vector, i.e., the average of 91 percent, 81 percent, and 43 percent using the example beat morphology matches described above.

In this way, the method of delivering a pacing therapy in a cardiac therapy device system in accordance with the present disclosure includes collecting a paced R-wave morphology associated with the cardiac signal sensed by a single far-field sensor formed by electrodes of a single pass coronary sinus lead, or each of multiple far-field sensing vectors formed by electrodes of a single pass coronary sinus lead, compares the R-wave morphology of each vector(s) to an intrinsic R-wave morphology template and generates a paced beat morphology match for the current paced beat in response to the comparing, and determines whether there is a certain degree of dissimilarity between the sensed R-wave or evoked response associated with the delivered pacing therapy and an intrinsic R-wave that would indicate that the delivered pacing therapy is effectively pacing the patient's heart.

In this way, the present disclosure sets forth a method of adaptive cardiac resynchronization in a system utilizing only a single pass coronary sinus lead that includes utilizing far-field electrogram morphology to verify LV capture and verify proper synchronization with the other chambers of the heart, more specifically fusion with intrinsic conduction. If the morphology analysis suggests loss of LV capture the device increases the pacing output or switches stimulation to a different pacing electrode pair/vector. On the other hand, if the morphology analysis suggests loss of synchronization, the device adjusts pacing timing. By only using a single-pass, left-sided, DDD lead, the cardiac therapy device system of the present disclosure reduces the risk of the occurrence of complications due to there being less device hardware being introduced within the patient's body compared to current therapy systems for delivering CRT that typically include a right atrial lead, a right ventricle lead, and a left ventricle lead.

The techniques described in this disclosure, including those attributed to the IMD 12, processor 70, the programmer 22, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A method for delivering a left ventricular (LV) cardiac pacing therapy to a patient, comprising:
    delivering the LV cardiac pacing therapy via an electrode of a plurality of electrodes, the plurality of electrodes positioned on one or both of a single-pass coronary sinus lead and a housing, the single-pass coronary sinus lead proximate to both an atrium and a ventricle, the single pass coronary sinus lead comprising a single implanted lead, the plurality of electrodes comprising a right atrial electrode located in the right atrium, a left ventricular electrode located proximate the left ventricle, and a housing electrode located on the housing;
    sensing far-field cardiac signals via one or more far-field sensing vectors formed between any combination of the right atrial electrode, the left ventricular electrode, and the housing electrode;
    determining a beat morphology corresponding to the far-field cardiac signals sensed for each of the far-field sensing vectors to generate corresponding far-field beat morphologies;
    determining a beat morphology match between each of the far-field beat morphologies and an intrinsic beat morphology template;
    determining one of loss of LV capture, pseudo fusion and loss of synchrony in response to the determined beat morphology match;
    performing one of a loss of capture adjustment, a pseudo fusion adjustment, and a resynchronization adjustment in response to the determined one of loss of LV capture, pseudo fusion, and loss of synchrony in response to the determined beat morphology match to generate an adjusted LV cardiac pacing therapy; and
    delivering the adjusted LV cardiac pacing therapy via an electrode of the plurality of electrodes.

2. The method of claim 1, further comprising determining whether the beat morphology match is one of greater than a loss of capture threshold, not greater than the loss of capture threshold and greater than a pseudo fusion threshold, and less than a loss of synchronization score.

3. The method of claim 2, wherein the loss of capture threshold is a 90 percent beat morphology match, the pseudo fusion threshold is an 80 percent beat morphology match, and the loss of synchronization threshold is a 20 percent beat morphology match score.

4. The method of claim 2, further comprising one of increasing a pacing output of the delivered LV cardiac pacing therapy and switching the delivery of the LV cardiac pacing therapy from the electrode of the plurality of electrodes to another electrode of the plurality of electrodes in response to the beat morphology match being greater than the loss of capture threshold.

5. The method of claim 2, further comprising decreasing an AV delay associated with the delivered LV cardiac pacing therapy in response to the beat morphology match not being greater than the loss of capture threshold and being greater than the pseudo fusion threshold.

6. The method of claim 2, further comprising increasing an AV delay associated with the delivered LV cardiac pacing therapy in response to the beat morphology match being less than the loss of synchronization threshold.

7. The method of claim 2, further comprising:
    determining whether the LV cardiac pacing therapy is delivered within one of a P-wave threshold and an R-wave threshold; and
    adjusting an AV delay associated with the delivered LV cardiac pacing therapy in response to the LV cardiac pacing therapy being delivered within one of the P-wave threshold and the R-wave threshold.

8. The method of claim 7, wherein the P-wave threshold is 30 ms and the R-wave threshold is between 30 ms and 40 ms.

9. The method of claim 2, further comprising determining whether to update the intrinsic beat morphology template in response to one of the beat morphology match being greater than the loss of capture threshold, not greater than the loss of capture threshold and greater than the pseudo fusion threshold, and less than the loss of synchronization score, and in response to the beat morphology match being neither one of greater than the loss of capture threshold, greater than the loss of capture threshold and greater than the pseudo fusion threshold, and less than the loss of synchronization score.

10. An implantable medical device system for delivering a left ventricular (LV) cardiac pacing therapy to a patient, comprising:
    an implantable medical device housing;
    a single implanted lead comprising a single-pass coronary sinus lead capable of being electrically couple to the implantable medical device housing;
    a plurality of electrodes positioned along one or both of the single-pass coronary sinus lead and the medical device housing, the single-pass coronary sinus lead proximate to both an atrium and a ventricle, the plurality of electrodes configured to sense a far-field cardiac signal of the patient and deliver the LV cardiac pacing therapy, the plurality of electrodes comprising a right atrial electrode located in the right atrium, a left ventricular electrode located proximate the left ventricle, and a housing electrode located on the housing; and
    a processor positioned within the implantable medical device housing and configured to sense far-field cardiac signals via one or more far-field sensing vectors formed between any combination of the right atrial electrode, the left ventricular electrode, and the housing electrode, determine a beat morphology corresponding to the far-field cardiac signals sensed for each of the far-field sensing vectors to generate corresponding far-field beat morphologies, determine a beat morphology match between each of the far-field beat morphologies and an intrinsic beat morphology template, determine one of loss of LV capture, pseudo fusion and loss of synchrony in response to the determined beat morphology match, perform one of a loss of capture adjustment, a pseudo fusion adjustment, and a resynchronization adjustment in response to the determined one of loss of LV capture, pseudo fusion, and loss of synchrony in response to the determined beat morphology match to generate an adjusted LV cardiac pacing therapy, and deliver the adjusted LV cardiac pacing therapy via an electrode of the plurality of electrodes.

11. The implantable medical device system of claim 10, wherein the processor is configured to determine whether the beat morphology match is one of greater than a loss of capture threshold, not greater than the loss of capture threshold and greater than a pseudo fusion threshold, and less than a loss of synchronization score.

12. The implantable medical device system of claim 11, wherein the loss of capture threshold is a 90 percent beat morphology match, the pseudo fusion threshold is an 80 percent beat morphology match, and the loss of synchronization threshold is a 20 percent beat morphology match score.

13. The implantable medical device system of claim 11, wherein the processor is configured to perform one of increasing a pacing output of the delivered LV cardiac pacing therapy and switching the delivery of the LV cardiac pacing therapy from the electrode of the plurality of electrodes to another electrode of the plurality of electrodes in response to the beat morphology match being greater than the loss of capture threshold.

14. The implantable medical device system of claim 11, wherein the processor is configured to decrease an AV delay associated with the delivered LV cardiac pacing therapy in response to the beat morphology match not being greater than the loss of capture threshold and being greater than the pseudo fusion threshold.

15. The implantable medical device system of claim 11, wherein the processor is configured to increase an AV delay associated with the delivered LV cardiac pacing therapy in response to the beat morphology match being less than the loss of synchronization threshold.

16. The implantable medical device system of claim 11, wherein the processor is configured to determine whether the LV cardiac pacing therapy is delivered within one of a P-wave threshold and an R-wave threshold, and adjust an AV delay associated with the delivered LV cardiac pacing therapy in response to the LV cardiac pacing therapy being delivered within one of the P-wave threshold and the R-wave threshold.

17. The implantable medical device system of claim 16, wherein the P-wave threshold is 30 ms and the R-wave threshold is between 30 ms and 40 ms.

18. The method of claim 11, wherein the processor is configured to determine whether to update the intrinsic beat morphology template in response to one of the beat morphology match being greater than the loss of capture threshold, not greater than the loss of capture threshold and greater than the pseudo fusion threshold, and less than the loss of synchronization score, and in response to the beat morphology match being neither one of greater than the loss of capture threshold, greater than the loss of capture threshold and greater than the pseudo fusion threshold, and less than the loss of synchronization score.

19. A non-transitory computer readable medium storing instructions which cause an implantable medical device to perform a method, the method comprising:
  delivering the LV cardiac pacing therapy via an electrode of a plurality of electrodes, the plurality of electrodes positioned on one or both of a single-pass coronary sinus lead and a housing, the single-pass coronary sinus lead proximate to both an atrium and a ventricle, the single pass coronary sinus lead comprising a single implanted lead, the plurality of electrodes comprising a right atrial electrode located in the right atrium, a left ventricular electrode located proximate the left ventricle, and a housing electrode located on the housing;
  sensing far-field cardiac signals via one or more far-field sensing vectors formed between any combination of the right atrial electrode, the left ventricular electrode, and the housing electrode;
  determining a beat morphology corresponding to the far-field cardiac signals sensed for each of the far-field sensing vectors to generate corresponding far-field beat morphologies;
  determining a beat morphology match between each of the far-field beat morphologies and an intrinsic beat morphology template;
  determining one of loss of LV capture, pseudo fusion and loss of synchrony in response to the determined beat morphology match;
  performing one of a loss of capture adjustment, a pseudo fusion adjustment, and a resynchronization adjustment in response to the determined one of loss of LV capture, pseudo fusion, and loss of synchrony in response to the determined beat morphology match to generate an adjusted LV cardiac pacing therapy; and
  delivering the adjusted LV cardiac pacing therapy via an electrode of the plurality of electrodes.

* * * * *